United States Patent
Castleman

[11] Patent Number: 5,968,046
[45] Date of Patent: Oct. 19, 1999

[54] PROVISIONAL FIXATION PIN

[75] Inventor: David Castleman, Bartlett, Tenn.

[73] Assignee: Smith & Nephew, Inc., Del.

[21] Appl. No.: 09/090,117

[22] Filed: Jun. 4, 1998

[51] Int. Cl.⁶ .................................................. A61B 17/58
[52] U.S. Cl. ............................................. 606/73; 606/69
[58] Field of Search ................................. 606/69, 70, 71, 606/73

[56] References Cited

U.S. PATENT DOCUMENTS

| 5,129,899 | 7/1992 | Small et al. | 606/61 |
| 5,433,719 | 7/1995 | Pennig | 606/73 |
| 5,676,667 | 10/1997 | Hausman | 606/69 |
| 5,700,267 | 12/1997 | Urbanski | 606/86 |
| 5,702,396 | 12/1997 | Hoenig et al. | 606/69 |

OTHER PUBLICATIONS

Aline™ Anterior Cervical Plating System, Surgical Technique, Smith & Nephew Orthopaedics Catalog, 3pgs.

Primary Examiner—Michael Buiz
Assistant Examiner—Daphna Shai
Attorney, Agent, or Firm—Garvey, Smith, Nehrbass & Doody, LLC

[57] ABSTRACT

A method and apparatus for reducing a fracture provides a provisional fixation pin to provisionally affix the bone plate to the bone prior to the installation of the bone plate with permanent attachment, such as bone screws. The method and apparatus of the present invention will maintain some reduction without significantly compromising the bone. The method utilizes a provisional fixation pin having an upper or proximal unthreaded shaft section and a lower externally threaded shaft section. A cutting tip is provided at the extreme distal end of the fixation pin. In between the proximal and distal sections is an enlarged diameter section that has an annular surface sized and shaped to conform to the countersunk surface of openings in the bone plate.

22 Claims, 4 Drawing Sheets

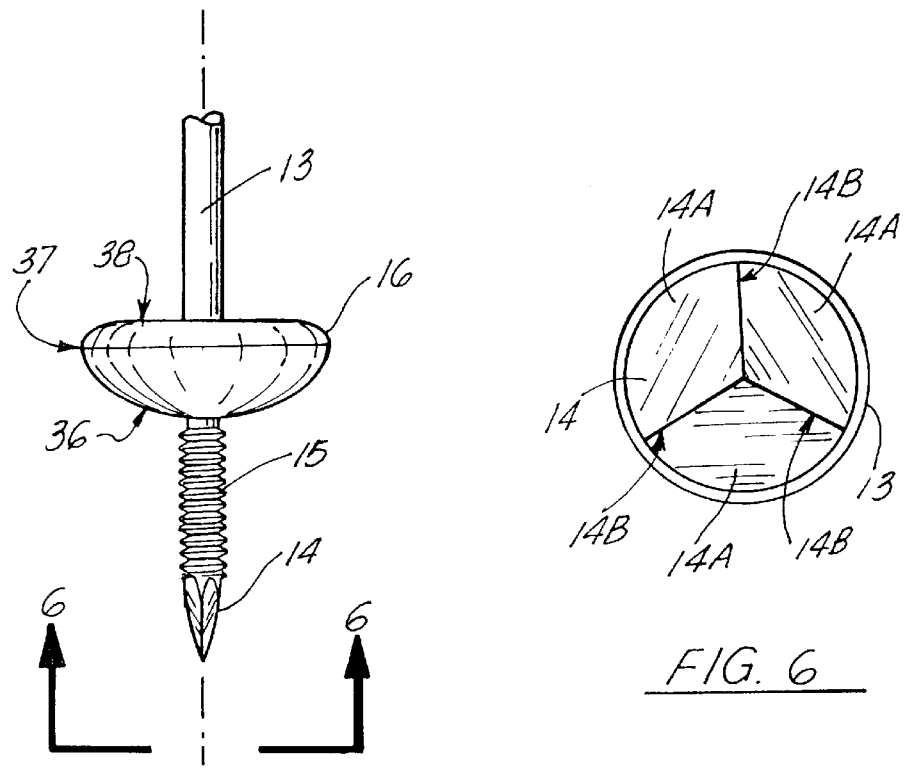
FIG. 5
FIG. 6
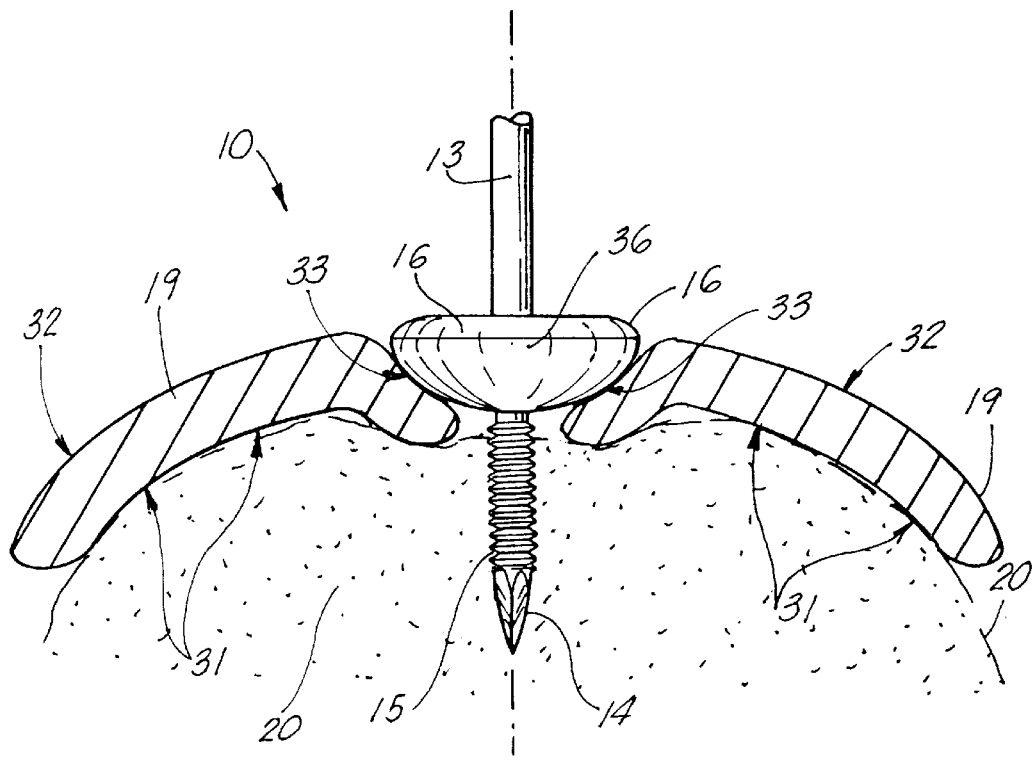
FIG. 7

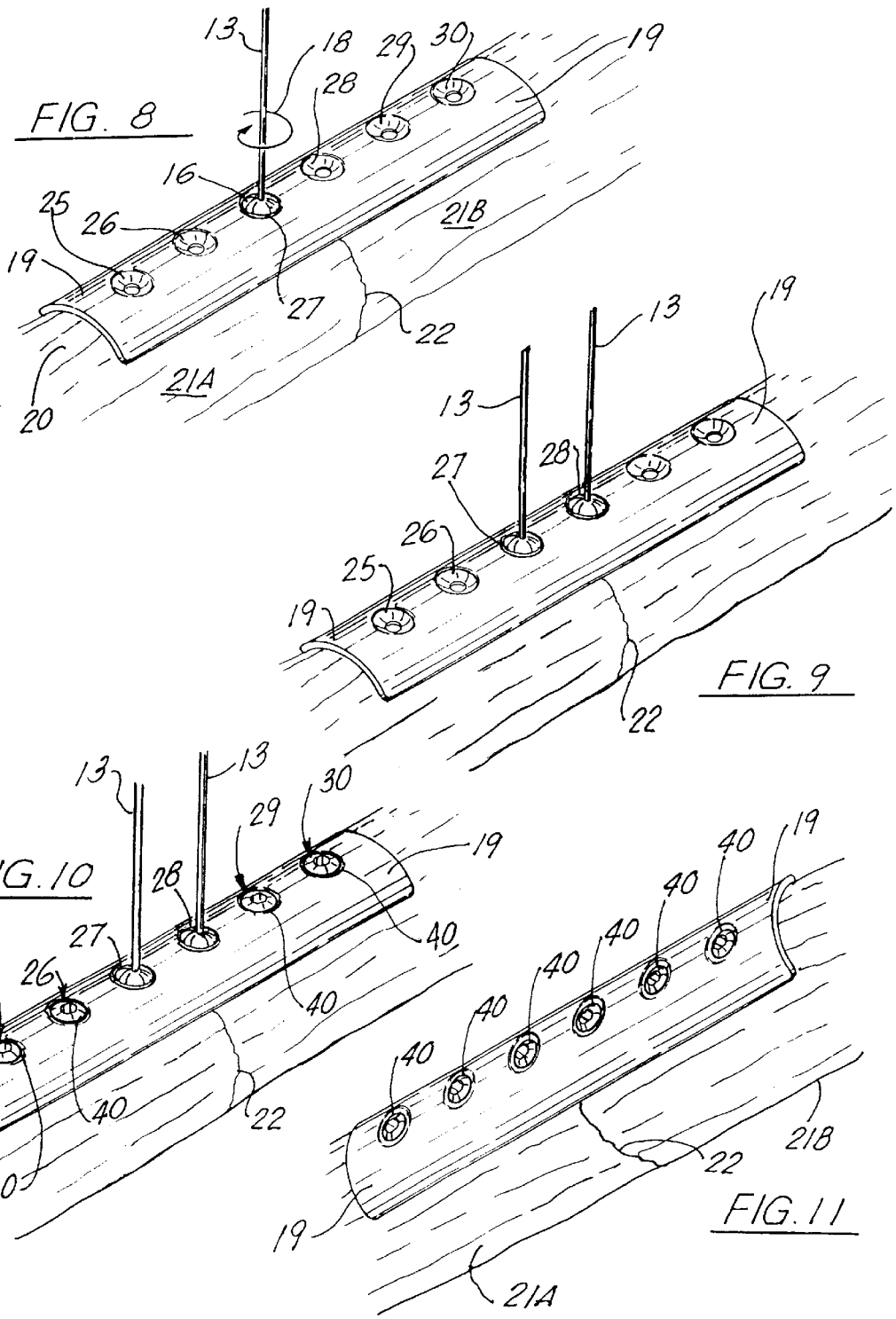

PROVISIONAL FIXATION PIN

CROSS-REFERENCE TO RELATED APPLICATIONS

Not applicable.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to a method and apparatus for reducing a patient's fractured bone using an elongated bone plate that has a plurality of openings therethrough, the openings having countersunk portions that correspond in shape to the countersunk head portion of a bone screw used to affix the bone plate to the patient's tissue and improved provisional fixation pins that preliminarily affix the plate in a selected position. Even more particularly, the present invention relates to an improved method and apparatus for reducing a patient's fractured bone at a fracture site wherein provisional fixation pins are used to preliminarily position the bone plate prior to permanent attachment with bone screws, each provisional fixation pin featuring a lower drilling tip portion and an enlarged diameter middle section having a surface that fits the countersunk openings of the bone plate. The lower drilling tip portion is smaller in diameter than the final bone screws to be used for permanent affixation.

2. General Background of the Invention

Bone plates have long been used to reduce and stabilize a patient's fractured bone at a fracture site. Bone plates are often shaped to conform to the patient's bone, having a concave rear surface shaped to fit a long bone of the leg or arm. Presently, many bone plates provide openings that include countersunk surfaces that are sized and shaped to conform to the countersunk head bone screws used to attach the bone plate to the patient's bone tissue.

One of the problems with the placement of a bone plate during surgery is that the bone screws used in cooperation with the plate typically have a diameter and distal tip that are imprecise when trying to perfectly place the screw. Often times, the surgeon misplaces a bone screw by a millimeter or two so that the plate is misaligned when all of the bone screws are finally implanted through the bone plate and into the patient's underlying bone tissue. This problem of preliminary fixation of bone plates has been recognized in the art.

Bone clamps are the standard method of provisionally attaching a plate to the bone prior to placing the bone screws through the plate. At least one spinal cervical plate for use in vertebral interbody fusions provides series of smaller holes in addition to the larger screw holes. These smaller holes accept pins that temporarily position the plate prior to placement of the larger bone screws. Clamps are not practical in the cervical area of the body. The limitations of these pins, however, is that they have no threads and must be driven in. This dictates that such pins can only be used to position the plate and not to hold the fracture reduced (i.e., hold the bone to the plate along the axis of the pin). In the case of a comminuted fracture with small bone fragments, attempting to drive the pins in instead of screwing them in may further displace the fragment from the plate.

There has been some discussion of standard bone plates with smaller holes similar to those in the spinal plates. These holes are used with standard K-Wires that have no shoulder and only position the plate, not affix it to the bone. Another draw back to this prior art methods is that it requires a special corresponding plate with small holes to accommodate the pins and cannot be used with standard bone plates.

One patent that discusses fixation pins for small bone fragments is the Pennig Pat. No. 5,433,719, entitled "Fixation Pin For Small-Bone Fragments". The '719 patent contemplates an implantable fixation pin for retaining small bone fragments in an osteosynthesis procedure. The pin comprises a smooth-walled shank portion and an adjoining threaded portion, wherein a step-down conical shoulder is formed between the shank portion and the threaded portion.

The Hausman Pat. No. 5,676,667 discloses a fixation plate for fixing the position of a fractured bone. The plate includes an elongated rigid plate having a plurality of first aperture spaced along the length of the plate. The first apertures are arranged and sized to receive threaded fasteners for fastening the plate to the bone on both sides of the fracture. The fixation plate also includes a plurality of second apertures spaced along the length of the plate. The second apertures, which are smaller than the first apertures, are arranged and sized to receive tacks to temporarily attach the plate to the bone on both sides of the fracture.

A publication that discusses the reduction of bone using plates and illustrates bone clamps is the Smith & Nephew Orthopaedics Information Catalog entitled "Aline™ Anterior Cervical Plating System".

BRIEF SUMMARY OF THE INVENTION

The present invention is directed to a device that temporarily (provisionally) affixes a bone plate to the bone prior to the installation of the permanent attachment method, such as bone screws that will maintain some reduction without significantly comprising the bone.

The present invention thus provides a method of reducing a patient's fractured bone at a fracture site by preliminarily positioning a bone plate at the fracture site and at a selected provisional position.

The bone plate has a plurality of countersunk surfaces next to openings that receives bone screws such as the type that are commercially available having countersunk head portions.

The bone plate is secured to the patient's bone tissue at the fracture site with a plurality of provisional fixation pins.

Each of the fixation pins has a threaded distal end portion that passes through a selected opening in the bone plate and into underlying bone tissue.

The provisional fixation pins each provide an enlarged diameter portion having a surface that is shaped to fit the countersunk surfaces of the openings in the bone plate. Each of the provisional fixation pins has an upper unthreaded proximal section that can be attached to a driver such as a drill or like driver tool instrument.

The plurality of fixation pins are used to preliminarily hold the bone plate in a preliminary position. This enables a surgeon to confirm that placement is proper before permanently affixing the bone plate with bone screws.

The provisional fixation pin and its enlarged diameter section with the countersunk surface maintains some reduction without significantly comprising the bone. The lower end portion of the provisional fixation pin is relatively small in diameter, having a diameter that is smaller than the diameter of the shank of the bone screw that will eventually permanently attach the bone plate to the bone tissue.

With the method of the present invention, each provisional fixation pin is removed once plate position is proper. A bone screw is then implanted at the same location and in the same "pilot hole" formed by the provisional fixation pin.

A plurality of provisional fixation pins hold the bone plate in position. They maintain that position while the surgeon inserts conventional bone screws into openings of the plate that are not occupied. Once the plate is firmly and permanently anchored with conventional bone screws, the fixation pins can be removed one at a time and replaced with bone screws.

The present invention thus provides an improved bone plate apparatus for repairing a patient's fractured bone at the fracture site.

The apparatus includes a bone plate having upper and lower surfaces and a plurality of openings that include countersunk surfaces. These openings extend through the bone plate, the countersunk surfaces communicating with the upper or proximal surface of the bone plate.

A plurality of provisional bone pins are provided that respectively fit the plurality of openings, each bone pin having a threaded distal section with a drilling tip and a proximal section. An enlarged diameter section is positioned in between the proximal and distal sections.

The enlarged diameter section can include a convex annular surface that closely conforms in size and shape to the countersunk surface of each opening through the bone plate.

A plurality of larger diameter bone screws replace the provisional fixation pins, each bone screw having a head and a threaded shank. The diameter of the threaded shank is larger than the diameter of the distal section of the provisional bone pin.

The head of each bone screw is about the same diameter as the enlarged diameter section of the provisional bone pin.

BRIEF DESCRIPTION OF THE DRAWINGS

For a further understanding of the nature, objects, and advantages of the present invention, reference should be had to the following detailed description, read in conjunction with the following drawings, wherein like reference numerals denote like elements and wherein:

FIG. 5 is a partial elevational view of the preferred embodiment of the apparatus of the present invention;

FIG. 6 is a distal view taken along lines 6—6 of FIG. 5;

FIG. 7 is a fragmentary partial section elevational view illustrating the method and apparatus of the present invention;

FIG. 8 is a perspective view of the preferred embodiment of the apparatus of the present invention, and illustrating the first step of the method of the present invention;

FIG. 9 is a perspective view of the preferred embodiment of the apparatus of the present invention, and illustrating the second step of the method of the present invention;

FIG. 10 is a perspective view of the preferred embodiment of the apparatus of the present invention illustrating the third step of the method of the present invention; and FIG. 11 is a perspective view of the preferred embodiment of the apparatus of the present invention, and illustrating the fourth step of the method of the present invention.

DETAILED DESCRIPTION OF THE INVENTION

Figure 1:
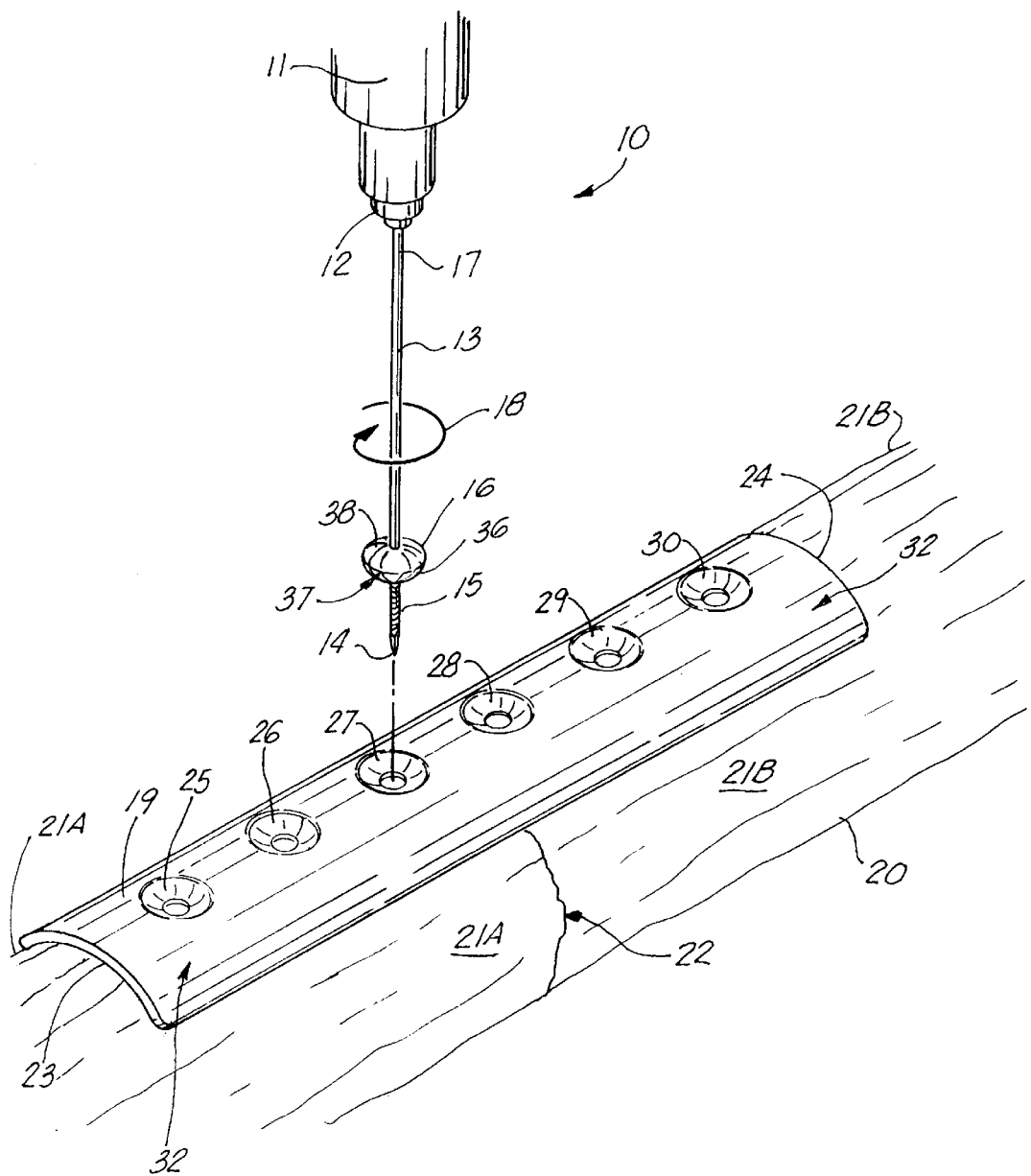
FIG. 1 is a perspective of the preferred embodiment of the apparatus of the present invention.

FIGS. 1–7 show the preferred embodiment of the apparatus of the present invention designated generally by the numeral 10 in FIGS. 1 and 7. In FIG. 1, provisional fixation apparatus 10 is shown at a fracture site 22 in patient's bone tissue 20. The bone tissue 20 includes segments 21A, 21B on opposite sides of fracture 22.

A drill 11 having a drill chuck 12 is used to insert a provisional fixation pin 13. In FIG. 1, the provisional fixation pin 13 includes an upper or proximal section 17 that is unthreaded, an enlarged diameter middle section 16, and a lower or distal section 15 having cutting tip 14. In FIGS. 1, 5, and 6, the provisional fixation pin 13 has a distal section 15 that is externally threaded. Cutting tip 14 can include three flat surfaces 14A and three cutting blades 14B.

During placement of the provisional fixation pin 13, the drill 11 and drill chuck 12 rotate in the direction of curved arrow 18 so that the cutting tip 14 cuts into the underlying bone tissue 20 embedding the externally threaded distal section 15 as shown in FIG. 7.

Figure 2:
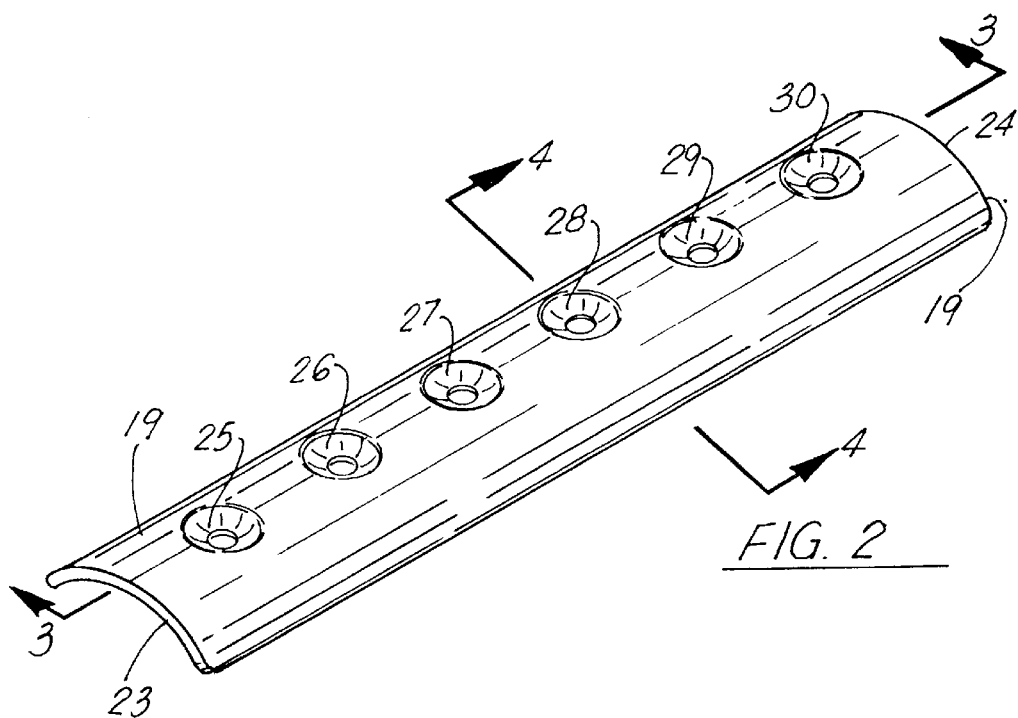
FIG. 2 is a partial perspective view of the preferred embodiment of the apparatus of the present invention.
Figure 3:
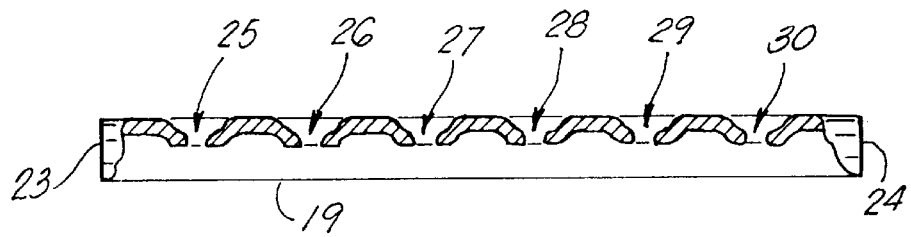
FIG. 3 is a sectional view taken along lines 3—3 of FIG. 2.
Figure 4:
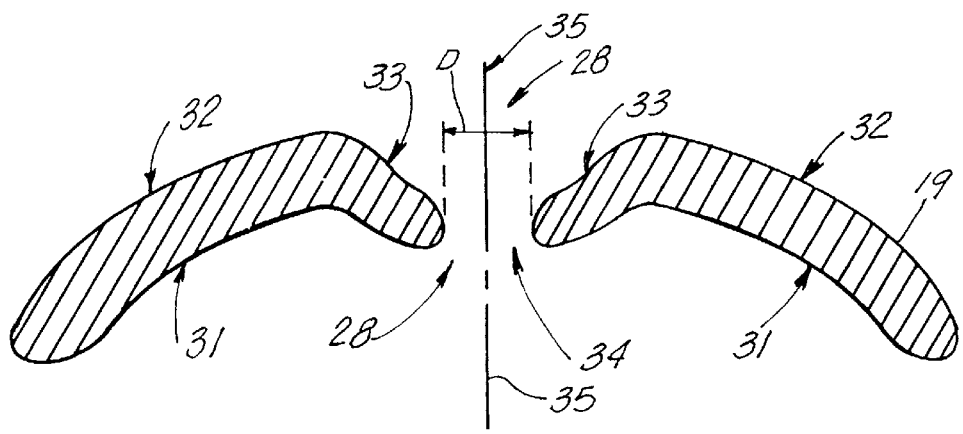
FIG. 4 is a sectional view taken along lines 4—4 of FIG. 2.

The provisional fixation pin 13 provides a lower externally threaded distal section 15 of a smaller diameter that is much smaller in diameter than the diameter D of the circular openings 14 in bone plate 19. In FIGS. 2–4, bone plate 19 has end portions 23, 24. In FIG. 4, a sectional view of bone plate 19 shows that there are a plurality of openings 25–30, each of which includes a circular opening 34 and a countersunk surface portion 33. The diameter D shown in FIG. 4 is of a diameter of 7 mm for example, while the diameter of external threaded distal section 15 is about 1.5 mm in diameter. This smaller diameter enables the surgeon to provisionally affix the bone plate 19 to the underlying tissue 20 without invading the bone tissue with a very large opening such as is formed by a conventional bone screw 39 having a shank diameter closely approaching the diameter "D" of opening 34 in FIG. 4.

Each of the openings 25–30 of bone plate 19 will eventually be occupied by a bone screw 39 having a countersunk head 40 portion. Prior to the placement of bone screws 39, the provisional fixation pins 13 of the present invention enable some reduction without significantly compromising the underlying bone tissue 20.

Bone plate 19 has end portions 23 and 24. The bone plate 19 also provides an inner concave surface 31 and an outer convex surface 32. Each of the openings 25–30 includes the circular opening 34 that communicates with both the upper convex surface 32 and the lower concave surface 31. The countersunk portion 33 communicates only with the upper convex surface 32. During use, both the provisional fixation pin 13 and a bone screw will preferably track the path of central axis 35 of opening 28 (see FIG. 4) or the central axis of any of the other selected openings 25–30.

In FIG. 5, the enlarged diameter section 16 of provisional fixation pin 13 has a lower convexly shaped annular surface 36. In FIG. 7, surface 36 conforms to and fits surface 33 of bone plate 19. Annular line 37 defines a border in between the lower annular surface 36 and upper annular surface 38 of enlarged diameter section 16.

In FIGS. 8–11, the method of the present invention is shown. The bone plate 19 has been placed in a provisional selected position at fracture site 22. In FIG. 8, five of the openings 25, 26, 28, 29, and 30 are unoccupied. In this position, two of the openings 27 and 28 are next to but on opposite sides of the fracture site 22 as shown. A single provisional fixation pin 13 has been inserted by rotating the pin 13 in the direction of arrow 18. Rotation continues until the large diameter section 16 occupies the opening 27, the annular surface 36 abutting and conforming to the countersunk surface 33 of the selected bone plate opening 25, 26, 27, 28, 29, 30.

The following table lists the parts numbers and parts descriptions as used herein and in the drawings attached hereto.

PARTS LIST

| Part Number | Description |
| --- | --- |
| 10 | provisional fixation apparatus |
| 11 | drill |
| 12 | drill chuck |
| 13 | provisional fixation pin |
| 14 | drill distal tip |
| 14A | flat surface |
| 14B | cutting edge |
| 15 | externally threaded distal section |
| 16 | enlarged section |
| 17 | unthreaded proximal section |
| 18 | curved arrow |
| 19 | bone plate |
| 20 | patient's bone tissue |
| 21A | bone segment |
| 21B | bone segment |
| 22 | fracture site |
| 23 | end portion |
| 24 | end portion |
| 25 | opening |
| 26 | opening |
| 27 | opening |
| 28 | opening |
| 29 | opening |
| 30 | opening |
| 31 | concave surface |
| 32 | convex surface |
| 33 | countersunk surface |
| 34 | circular opening |
| 35 | central axis |
| 36 | lower annular surface |
| 37 | annular line |
| 38 | upper annular surface |
| 39 | bone screw |
| 40 | head |

The foregoing embodiments are presented by way of example only; the scope of the present invention is to be limited only by the following claims.

I claim:

1. A method of reducing a patient's fractured bone at a fracture site comprising the steps of:
   a) preliminarily positioning a bone plate at the fracture site and at a selected provisional position, wherein the bone plate has a plurality of countersunk openings for receiving bone screws with countersunk head portions;
   b) securing the bone plate to the patient's bone tissue at the fracture site with a plurality of provisional fixation pins, each having a threaded distal portion that passes through a selected countersunk opening and into underlying bone tissue;
   c) wherein the provisional fixation pins in step "b" each have an enlarged diameter portion that engages the countersunk opening of the bone plate;
   d) using the plurality of provisional fixation pins to preliminarily hold the bone plate in the preliminary position of step "a"; and
   e) permanently affixing the bone plate to the patient's bone tissue at the provisional fixation site using bone screws that are implanted by placement through the countersunk openings of the bone plate, wherein each provisional fixation pin is removed and at least some of said provisional fixation pins are replaced with a bone screw.

2. A method of reducing a patient's fractured bone at a fracture site comprising the steps of:
   a) preliminarily positioning a bone plate at the fracture site and at a selected provisional position, wherein the bone plate has a plurality of countersunk openings for receiving bone screws with countersunk head portions;
   b) securing the bone plate to the patient's bone tissue at the fracture site with a plurality of provisional fixation pins, each having a threaded distal portion that passes through a selected countersunk opening and into underlying bone tissue;
   c) wherein the provisional fixation pins in step "b" each have an enlarged diameter portion shaped to fit the countersunk opening of the bone plate;
   d) using the plurality of provisional fixation pins to preliminarily hold the bone plate in the preliminary position of step "a"; and
   e) permanently affixing the bone plate to the patient's bone tissue at the provisional fixation site using bone screws that are implanted by placement through the countersunk openings of the bone plate that are not occupied by provisional fixation pins,
   f) wherein in step "e" a provisional fixation pin is removed from an opening in steps "d" and "e" before a bone screw is implanted in step "e".

3. A method of reducing a patient's fractured bone at a fracture site comprising the steps of:
   a) preliminarily positioning a bone plate at the fracture site and at a selected provisional position, wherein the bone plate has a plurality of countersunk openings for receiving bone screws with countersunk head portions;
   b) securing the bone plate to the patient's bone tissue at the fracture site with a plurality of provisional fixation pins, each having a threaded distal portion that passes through a selected countersunk opening and into underlying bone tissue;
   c) wherein the provisional fixation pins in step "b" each have an enlarged diameter portion shaped to fit the countersunk opening of the bone plate;
   d) using the plurality of provisional fixation pins to preliminarily hold the bone plate in the preliminary position of step "a"; and
   e) permanently affixing the bone plate to the patient's bone tissue at the provisional fixation site using bone screws that are implanted by placement through the countersunk openings of the bone plate that are not occupied by provisional fixation pins; and
   f) wherein the provisional fixation pins have a lower end below the enlarged diameter portion that is much smaller in diameter than the bone screw of step "e", and further comprising the steps of removing a provisional pin from an opening and inserting a bone screw into the bone tissue opening that was formed in step "d".

4. A method of reducing a patient's fractured bone at a fracture site comprising the steps of:
   a) preliminarily positioning a bone plate at the fracture site and at a selected provisional position, wherein the bone plate has a plurality of countersunk openings for receiving bone screws with countersunk head portions;
   b) securing the bone plate to the patient's bone tissue at the fracture site with a plurality of provisional fixation pins, each having a threaded distal portion that passes through a selected countersunk opening and into underlying bone tissue;
   c) wherein the provisional fixation pins in step "b" each have an enlarged diameter portion shaped to fit the countersunk opening of the bone plate;
   d) using the plurality of provisional fixation pins to preliminarily hold the bone plate in the preliminary position of step "a"; and
   e) permanently affixing the bone plate to the patient's bone tissue at the provisional fixation site using bone screws that are implanted by placement through the countersunk openings of the bone plate, wherein each provisional fixation pin is removed and at least some of said provisional fixation pins are replaced with a bone screw;
   f) wherein in step "c" the enlarged diameter portion has an annular surface that is shaped to fit the same countersunk openings of the bone plate that are receptive of the bone screws; and
   g) wherein the enlarged diameter portion corresponds generally in size and shape to the countersunk head portions of the bone screws used in steps "a" and "e".

5. A method of reducing a patient's fractured bone at a fracture site comprising the steps of:
   a) preliminarily positioning a bone plate at the fracture site and at a selected provisional position, wherein the bone plate has a plurality of countersunk openings for receiving bone screws with countersunk head portions;
   b) securing the bone plate to the patient's bone tissue at the fracture site with a plurality of provisional fixation pins, each having a threaded distal portion that passes through a selected countersunk opening and into underlying bone tissue;
   c) wherein the provisional fixation pins in steep "b" each have an enlarged diameter portion shaped to fit the countersunk opening of the bone plate;
   d) using the plurality of provisional fixation pins to preliminarily hold the bone plate in the preliminary position of step "a"; and
   e) permanently affixing the bone plate to the patient's bone tissue at the provisional fixation site using bone screws that are implanted by placement through the countersunk openings of the bone plate that are not occupied by provisional fixation pins;
   f) the method of claim 1 wherein in step "c" the enlarged diameter portion has an annular surface that is shaped to fit the countersunk opening of the bone plate; and
   g) wherein in step "c" the enlarged diameter portion has a domed annular proximal portion.

6. The method of claim 5, wherein the countersunk opening has a concave countersunk surface portion and further comprising the step of engaging the annular surface of the enlarged diameter portion with the countersunk surface portion.

7. The method of claim 6 wherein each countersunk opening includes a circular opening that is much larger in diameter than the threaded distal portion of the provisional fixation pins.

8. A bone plate apparatus for repairing a patient's fractured bone at a fracture site comprising:
   a) a bone plate having upper and lower surfaces and a plurality of countersunk openings through the plate, each opening including a countersunk surface that communicates with the upper surface of the plate;
   b) a plurality of provisional bone pins that respectively fit the plurality of openings, each pin having a threaded lower section with a drilling tip, an upper section, and an enlarged diameter section in between the upper and lower sections;
   c) the enlarged diameter section having a convex annular surface that closely conforms to the countersunk surface of an opening during use;
   d) a plurality of bone screws that have a head and a threaded shank, wherein the diameter of the threaded shank is much larger than the diameter of the distal section of the provisional bone pin; and
   e) wherein the head of each bone screw is about the same diameter as the enlarged diameter section of the provisional bone pin.

9. The bone plate apparatus of claim 8 wherein the diameter of the lower section of each provisional pin is about the same diameter as the diameter of the upper section.

10. The bone plate apparatus of claim 8 wherein the enlarged diameter section of one of said provisional bone pins is about the same size and shape as the head of one of said bone screws.

11. The bone plate apparatus of claim 8 wherein the provisional bone pin enlarged diameter section has a diameter that is many times greater than the diameter of the lower section.

12. The bone plate apparatus of claim 8 wherein the countersunk openings each include a concave countersunk surface that communicates with the upper bone plate surface and a generally circular opening that communicates with the lower bone plate surface.

13. The bone plate apparatus of claim 8 wherein the provisional bone pin distal section has a diameter of between 1 and 3 mm.

14. The bone plate apparatus of claim 8 wherein the provisional bone pin proximal section has a diameter of between 1 and 8 mm.

15. The bone plate apparatus of claim 8 wherein the enlarged diameter section has a diameter of between 4 and 10 mm.

16. The bone plate apparatus of claim 8 wherein the provisional bone pin distal section is externally threaded with a fine pitch thread pattern.

17. A method of reducing a patient's fractured bone at a fracture site comprising the steps of:
   a) preliminarily positioning a bone plate at the fracture site and at a selected provisional position, wherein the bone plate has a plurality of countersunk openings for receiving bone screws with countersunk head portions;
   b) securing the bone plate to the patient's bone tissue at the fracture site with a plurality of provisional fixation pins, each having a threaded distal portion that passes through a selected countersunk opening and into underlying bone tissue;
   c) wherein the provisional fixation pins in step "b" each have an enlarged diameter portion shaped to fit the countersunk opening of the bone plate and a proximal section, wherein the enlarged diameter portion closely conforms to the countersunk surface of a bone screw receptive opening;

d) using the plurality of provisional fixation pins to preliminarily hold the bone plate in the preliminary position of step "a"; and e) permanently affixing the bone plate to the patient's bone tissue at the provisional fixation site using bone screws that are implanted by placement through the countersunk openings of the bone plate wherein each provisional fixation pin is removed and at least some of said provisional fixation pins are replaced with a bone screw.

18. The method of claim 17 wherein the provisional fixation pins have a lower end below the enlarged diameter portion that is much smaller in diameter than the bone screw of step "e", and further comprising the steps of removing a provisional pin from an opening and inserting a bone screw into the bone tissue opening that was formed in step "d".

19. The method of claim 17 wherein in step "c" the enlarged diameter portion has a lower annular surface that is shaped to fit the countersunk opening of the bone plate.

20. The method of claim 17 wherein in step "c" the enlarged diameter portion has a domed annular proximal portion.

21. The method of claim 17, wherein the countersunk opening has a concave countersunk surface portion and further comprising the step of engaging the lower annular surface of the enlarged diameter portion with the countersunk surface portion.

22. The method of claim 17 wherein each countersunk opening includes a circular opening that is much larger in diameter than the lower end portion of the provisional fixation pins.

* * * * *